United States Patent [19]

Barabino et al.

[11] Patent Number: 4,931,274
[45] Date of Patent: Jun. 5, 1990

[54] COMPOSITION FOR THE EFFECTIVE TREATMENT OF SCALP DISEASES THAT DELIVERS MAGNESIUM ADSORBED IN ALUMINA SILICATE CLAYS TO AFFECTED SITES

[75] Inventors: William A. Barabino, North Reading; Robert J. Cross, Haverhill, both of Mass.

[73] Assignee: Physiological Research Associates, North Reading, Mass.

[21] Appl. No.: 233,033

[22] Filed: Aug. 17, 1988

Related U.S. Application Data

[63] Continuation-in-part of Ser. No. 835,443, Feb. 27, 1986, abandoned, which is a continuation of Ser. No. 606,975, May 4, 1984, abandoned.

[51] Int. Cl.$^5$ .................. A61K 7/06; A61K 7/48; A61K 9/08; A61K 33/12
[52] U.S. Cl. .................. 424/70; 424/DIG. 1; 424/DIG. 2; 424/DIG. 4; 514/256; 514/852; 514/863; 514/864; 514/873; 514/880; 514/881; 514/886; 514/887; 514/949; 514/951
[58] Field of Search .................. 514/863; 424/70

[56] References Cited

U.S. PATENT DOCUMENTS

| | | | |
|---|---|---|---|
| 3,937,822 | 2/1976 | DeLong et al. | 514/863 |
| 4,052,331 | 10/1977 | Dumoulin | 514/863 |
| 4,238,509 | 12/1980 | Evans | 514/863 |
| 4,424,234 | 1/1984 | Alderson et al. | 424/DIG. 5 |
| 4,810,496 | 3/1989 | Jensen | 514/863 |

FOREIGN PATENT DOCUMENTS

| | | | |
|---|---|---|---|
| 048153 | 3/1982 | European Pat. Off. | 514/863 |
| 0054701 | 6/1982 | European Pat. Off. | 514/859 |
| 2910473 | 9/1979 | Fed. Rep. of Germany | 514/859 |
| 717559 | 1/1932 | France | 514/863 |
| 969630 | 12/1950 | France | 514/863 |
| 137207 | 11/1978 | Japan | 514/859 |
| 0149208 | 11/1980 | Japan | 514/859 |
| 0112314 | 7/1982 | Japan | 514/859 |
| 169412 | 10/1982 | Japan | 424/70 |
| 7709273 | 2/1979 | Netherlands | 514/859 |
| 51517 | 7/1966 | Poland | 514/863 |
| 336019 | 5/1972 | U.S.S.R. | 514/863 |

OTHER PUBLICATIONS

Barr, Amer. Perf & Cosmetics, 2/1963, vol. 78, pp. 37 to 43 and 45.
Sperandio, Amer-Perf & Cosmetics, 10/1963, vol. 78.
Laporte, Amer. Perf & Cosmetics, 2/1970, vol. 85, No. 2, pp. 47 to 50.

Primary Examiner—Dale R. Ore
Attorney, Agent, or Firm—Richard C. Litman

[57] ABSTRACT

A composition for effectively treating dandruff, seborrheic dermatitis and scalp psoriasis comprising a combination of essential ingredients consisting of microfine particles of a clay mineral containing adsorbed magnesium, water, ethanol, sodium chloride and, optionally, minor amounts of glycerin and precipitated sulfur. The effectiveness of the method in treating such scalp diseases by topical application to the scalp epidermis is predicated on the capacity of the composition to release and deliver magnesium cations and hydroxyl anions to the causative sites and return the associated pathological cells to a normal morphology.

16 Claims, No Drawings

COMPOSITION FOR THE EFFECTIVE TREATMENT OF SCALP DISEASES THAT DELIVERS MAGNESIUM ADSORBED IN ALUMINA SILICATE CLAYS TO AFFECTED SITES

CROSS-REFERENCE TO RELATED APPLICATIONS

This application is a continuation-in-part of application Ser. No. 835,443 filed Feb. 27, 1986, which is a continuation of application Ser. No. 606,975 filed May 4, 1984, both now abandoned.

FIELD OF THE INVENTION

The present invention relates to a composition and a method for the effective treatment of scalp diseases. More particularly, this invention relates to a method of treating dandruff, seborrheic dermatitis and scalp psoriasis by topical application to the outer layer of the epidermis an effective amount of a composition which releases and delivers $Mg^{++}$ and $OH^-$ anions to the causative sites.

BACKGROUND OF THE INVENTION

Dandruff, seborrheic dermatitis and scalp psoriasis are symptomatic diseases resulting from a progessively increasing turnover rate of the epidermal cells of the scalp basale lamina and sebaceous glands. Sebum is known to be toxic to the epidermis onto which it flows. It is presently postulated that excessive sebum production from the pathological condition of multiple layers of growth cells in the periphery of the sebaceous gland increases this toxicity, resulting in premature necrosis and replacement of the scalp epidermis. Excessive sebum production will manifest itself as mounds or scales of exudate on the epidermis and as follicular plugs. Heretofore, these conditions could only be "treated" or "relieved" and prior compositions for treating and relieving these disease have been found to be without significant or permanent success.

The use of magnesium aluminum silicates and other alumina silicates in certain medical and health products as an inert ingredient is well-known. In 1982, the FDA attempted, via the Federal Register, to establish a monograph for non-prescription or over-the-counter (OTC) drug products for the control of dandruff, seborrheic dermatitis and psoriasis. It reviewed 85 ingredients contained in marketed products, 32 other ingredients classified as active, and 24 inactive ingredients. None of these reviewed ingredients were magnesium aluminum silicate. In an independent survey of all available OTC drug products for treatment of scalp diseases, comprising a total of 49 ingredients, only two listed magnesium aluminum silicate as ingredients. However, in the first case, sulfur, a keratolytic, was listed as the active ingredient and, in the second case, zinc pyrithione, a cytostatic, was the listed active ingredient.

The cation exchange capacity (CEC) of certain mineral clays is also generally well-documented and this property is utilized in many industrial and soil chemistry applications. However, there is no evidence in the literature of using the CEC of certain clays to release magnesium cations for physiological results. Further, there is no evidence in the literature to suggest that the delivery of such cations to the cytoplasm of covering epithelia would return certain pathological cells to normal, resulting in a normal mitotic rate. There is also no evidence in the literature to suggest that magnesium aluminum silicate may be used in any medicament other than as an inert ingredient, notwithstanding its swellability.

It is, accordingly, a primary object of the invention to provide a composition for the effective treatment of dandruff, seborrheic dermatitis and scalp psoriasis.

It is also a primary object of the invention to provide a composition which utilizes the cation exchange capacity of certain clay minerals to release and deliver magnesium cations ($Mg^{++}$) and hydroxyl anions ($OH^{31}$) to diseased dermal growth cells and diseased sebaceous gland cells to effectively treat epidermal and sebaceous disorder.

It is a further object of the invention to provide an effective method for returning pathological cells, characteristic of scalp diseases of the dermal basale lamina and peripheral cells of the sebaceous glands, to a normal conformation and a normal mitotic rate.

Another object of the present invention is to provide an orderly description of the varied and complex disciplines that contribute to and participate in the multifactorial mechanisms of the compositions provided by the invention.

SUMMARY OF THE INVENTION

The aforesaid objects are accomplished by the present invention wherein a novel composition for the effective treatment of scalp diseases is provided consisting of suitable amounts of microfine particles of a clay mineral containing adsorbed magnesium, water, ethanol and sodium chloride as the essential ingredients. The present invention also provides a method for effectively treating dandruff, seborrheic dermatitis and scalp psoriasis which comprises topically applying to the scalp epidermis an effective amount of the composition of the present invention. The complex interrelated chain of biogeochemical and chemical disciplines that are involved in returning the associated pathological cells of the described scalp diseases to a normal morphology will be described hereinafter in greater detail.

The above description, as well as further objects, features and advantages of the present invention, will be more fully appreciated by reference to the following detailed description.

DETAILED DESCRIPTION OF THE INVENTION

This invention provides a substantially non-toxic composition for the effective treatment of drandruff, seborrheic dermatitis and scalp psoriasis comprising an effective amount of a combination of essential ingredients consisting of microfine particles of a clay mineral containing adsorbed magnesium, water, ethanol and sodium chloride. As previously indicated, the therapeutic effectiveness of the present composition has been determined to reside in its capacity to release and deliver $Mg^{++}$ cations and $OH^-$ anions to certain pathological cells. Accordingly, each ingredient of the present composition is critical and actively contributes to and participates in the underlying biological and chemical mechanisms of the present invention, which will be described hereinafter in greater detail.

Generally, while any colloidal clay mineral or mixture thereof having magnesium cations exchangeable with hydrogen may be useful in accordance with the present invention, it is preferred to use microfine particles of certain alumina silicate clays containing adsorbed magnesium and having an average particle size of 0.5-3 microns. The alumina silicates may be reduced to the preferred particle size by grinding.

Many schemes of identification have been devised to identify a clay mineral from its physical and chemical properties. As documented herein, the Berzelius System is basically applicable whereby Class VIII, Silicates, is the class of interest. For audit purposes, the following description modifies and augments the Berzelius scheme to include crystalline form and layer structure as follows:

| | |
|---|---|
| 1.0 | Class VIII - Silicates |
| 2.0 | Subclass - Phyllosilicates |
| 3.0 | Group |
| | 3.1 Kaolin |
| | 3.2 Montmorillonite |
| |     3.2.1 Montmorillonite - High aluminum content having the formula: |
| (a) |         $Al_2Si_4O_{10}(OH)_2 \cdot xH_2O$ |
| |     3.2.2 Smectite - High magnesium content, end member formula: |
| (b) |         $(\tfrac{1}{2}Ca,Na)_{0.7}(Al,Mg,Fe)_4 Si,Al_8O_{20}(OH)_4 \cdot nH_2O$ |
| | 3.3 Clay Mica |
| | 3.4 Chlorite Series |
| 4.0 | Crystalline Structure |
| | 4.1 Dioctahedral (Gibbsite-type layer) |
| |     4.1.1 Two-layer structure |
| (c) |         4.1.1.1 Kaolinite - $Al_4Si_4O_{10}(OH)_8$ |
| |         4.1.1.N |
| |     4.1.2 Three-layer structure |
| (d) |         4.1.1.2 Montmorillonite - $Al_2Si_4O_{10}(OH)_2 \cdot xH_2O$ |
| |         4.1.1.N |
| | 4.2 Trioctahedral (Brucite type-layer) |
| |     4.2.1 Two-layer structure |
| (e) |         4.2.1.1 Chlorite-$Mg_5Al(AlSi_3O_{10})(OH)_8$ |

Although the minerals gibbsite $Al(OH)_3$ and brucite $MG(OH)_2$ are Class III minerals in the overall classification scheme they are unique in that their crystalline lattice is used to describe the clays of kaolinite, montmorillonite and chlorite. Gibbsite and brucite share anions between adjacent octahedra that results in a planar network often referred to as the octahedral layer. The Al-OH and Mg-OH layers in many phyllosilicates are correctly references as gibbsite-type or brucite-type layers, respectively. The gibbsite layer has a dioctahedral arrangement of two cations for each six OH anions; the brucite layer is trioctahedral having three cations for each six OH anions. The actual composition of montmorillonite, kaolinite and chlorite always deviate from the above-written formulas through substitutions in their structures, such as Mg for Al and Al for Si. This leads to a net negative charge on the layers which is compensated by additional or other cations such as $Mg^{++}$, $Ca^{++}$, $Na^+$ and/or $H_3O^+$ adsorbed between the layers. These loosely bound cations, because of their gibbsite-like and brucite-like location, are referred to as such in some Class VIII phyllosilicate clays. This characteristic is the causative factor of a Class VIII phyllosilicate having a cation exchange capacity (CEC) whereby cations in solution can be readily exchanged for brucite-like cations adsorbed on the component surface.

As shown by Formula (a) the classification of clay minerals in the montmorillonite group can be highly complex due to the component variances. It is generally accepted among those proficient in mineralogy that calcium and iron are the exchange ions in the cation exchange capacity of Class VIII phyllosilicates. As will be described later, instrument analysis will show $Mg^{++}$ is an exchangeable cation because its ionic radius of 0.66Å and its charge of +2 permits it to become an adsorbed brucite-type or gibbsite-type layer in certain alumina silicates.

The compositions of the present invention use the cation exchange capacity (CEC) of certain clay minerals by causing the replacement of the adsorbed magnesium with hydrogen in the gibbsite-type or brucite-type layers. Any magnesium alumina silicate may be suitable as the clay ingredient of the present composition, preferentially, one which generally meets the specifications for materials used in pharmaceutical and cosmetic composition. In a typical 100 ml laboratory preparation of the compositions of the present invention, this clay ingredient is present in amounts ranging from about 0.35-0.65 gm.

Distilled water may comprise about 16.5-27.5% by volume and ethanol may comprise about 53.5-89.5% by volume of a typical 100 ml preparation of the present composition.

It will be recognized by those skilled in the art that a mixture of alumina silicate clays, ethanol and water may react according to the following equations:

$$C_2H_5OH + H_2O \rightarrow CH_3-CH_2O^- + H_3O^+ \qquad (1)$$

or $$CH_3-CH_2-OH_2^+ + OH^- \qquad (2)$$

Partially working equation (1):
$$(MgAl_2Si_2O_7)_n + 2H_3O^+ \rightarrow H_2Al_2Si_2O_7 + 2H_2O + Mg^{++} \qquad (3)$$

Because $OH^-$ is a desired product in addition to the product release of $Mg^{++}$ cations in the overall working mechanisms of the compositions of the present invention, the competing reaction of Equation (3) in practice is substituted for the sequential formulation procedure of ethanol being added to the initial mixture of water and alumina silicate, resulting in dispersion according to the following equatin:

$$(MgAl_2Si_2O_7)_n \xrightarrow{\text{dispersion}} n\, MgAl_2Si_2O_7 \qquad (4)$$

The ionic bound magnesium of the gibbsite-type and brucite-type layers is the ionized and released into the aqueous phase resulting in strong basic Al-O sites remaining. The magnesium is also an exchangeable cation in accordance with the following equation:

$$MgAl_2Si_2O_7 \rightarrow Al_2Si_2O_7^{-2} + Mg^{+2}(aq) \qquad (5)$$

The Al-O sites are of sufficient strength to cause hydrolysis by the remaining $H^+$ from $H_2O$ molecules. This results in residual $OH^{31}$ ions which cause an increase in pH according to the following equation:

$$Al_2Si_2O_7 + 2H_2O \rightarrow Al_2Si_2O_5(OH)^2 + 2OH^- \qquad (6)$$

Having thus obtained the two desired products, $Mg^{+2}$ of Equation (5) and $OH^-$ of Equation (6), the remaining sodium chloride ingredient may be added. This ingredient may be preferably added as a 23.4% concentrated aqueous solution, which solution may comprise about 4.5-7.5% by volume of a typical 100 ml preparation of the present composition. The sodium chloride ingredient is used to not only inhibit the surface evaporation of ethanol, and to extend the viscosity gradient reactions between ethanol and water but also as an additional source of exchange ions in the form of sodium as will be described later.

A typical 100 ml preparation of a composition formulated in accordance with the sequential procedure described hereinabove can contain minor amounts of ingredients other than those already mentioned. It is preferable, for example, to optionally add an emollient, such as glycerin in an amount of about 1-3 drops. Also, a keratolytic agent, such as precipitated sulfur may be added if accelerated treatment is desired. The amount of precipitated sulfur, if added, usually comprises from about 0.15-2.5 gms, preferably 0.1-2.0 gms per 100 ml preparation.

Compositions according to the invention are particularly effective in returning pathological cells associated with dandruff, seborrheic dermatitis, scalp psoriasis and othe scalp diseases to a normal morphology by topical application to the outer epidermis. Three/four every-other-day topical applications will return diseased cells to normal conformation within 10/12 days. The process can be accelerated by the addition of precipitated sulfur. Compositions of the invention containing sulfur require only two/three applications with normal cellular conformations evident by the sixth/seventh day. The keratolytic properties of sulfur assist in the overall working mechanism by accelerating the removal of the seborrheic scale and follicular plug, thereby presenting a less obstructed pathway for the present compositions through the sebaceous canal and gland and into the basale lamina. As will be described in detail later, electron micrographs of in-vivo pre- and post-treated sections of human tissue treated with and without sulfur-containing compositions of the present invention have substantially identical results. The cure diagnosis of analyzed electron micrographs compares absolutely to the clinical results.

The invention is further illustrated by the following examples wherein all amounts of ingredients are given in percent by volume unless specifically stated otherwise.

EXAMPLE 1

This example illustrates a 100 ml laboratory preparation formulated from the following ingredients:

| Ingredient | | Amount |
|---|---|---|
| Alumina Silicate | $(MgAl_2Si_2O_7)_n$ | .5 gm |
| Water, distilled | $H_2O$ | 22.0%/v |
| Sodium Chloride-23.4% conc. (aq) | NaCl | 6.0%/v |
| Ethanol | $C_2H_5OH$ | 71.5%/v |
| Glycerin | $C_3H_8O_3$ | 2.0 drops |

Top to 100 ml with d. water

EXAMPLE 2

This example illustrates a sulfur-containing composition which is a 100 ml laboratory preparation formulated from the following ingredients:

| Ingredient | | Amount |
|---|---|---|
| Alumina Silicate | $(MgAl_2Si_2O_7)_n$ | .5 gm |
| Water, distilled | $H_2O$ | 22.0%/v |
| Sodium Chloride-23.4% conc. (aq) | NaCl | 6.0%/v |
| Ethanol | $C_2H_5OH$ | 71.5%/v |
| Glycerin | $C_3H_8O_3$ | 2.0 drops |
| Sulfur, precipitated | S | 0.1-2.0 gm |

Top to 100 ml. with d. water

EXAMPLE 3

This example illustrates a 100 ml preparation formulated from the following ingredients:

| Ingredient | | Amount |
|---|---|---|
| Alumina Silicate | $(MgAl_2Si_2O_7)_n$ | .5 gm |
| Water, distilled | $H_2O$ | 22.0%/v |
| Sodium Chloride-23.4% conc. (aq) | NaCl | 6.0%/v |
| Ethanol | $C_2H_5OH$ | 71.5%/v |

The topical application of the compositions of the present invention to the scalp epidermis of patients suffering from known diseases of dandruff, seborrheic dermatitis and scalp psoriasis results in the accelerated clinical disappearance of these scalp diseases. The initial discovery that the present compositions return pathological and hyperproliferation cells, associated with such scalp diseases of the dermal basale lamina and peripheral cells of the sebaceous glands to a normal conformation and a normal mitotic rate by the delivery of magnesium cations and hydroxyl anions to the cellular cytoplasm is considered to constitute new medical knowledge. This medical discovery and the further assessment that the magnesium cations absorbed on the surface of certain alumina silicate clays can be released under the fundamental criterion of particle size and hydrolysis was subsequently confirmed by the following Experimental Data.

EXPERIMENTAL DATA

A. Clay Analysis—The primary instruments used were the Scanning Electron Microscope (SEM) upon which an Energy Dispersive X-ray Spectroscope (EDX) was mounted. Those experienced in the art will know that the SEM will observe only the surface of the particles, a particularly important consideration relative to adsorbed elements. The EDX initially produces a qualitative spectrogram of the coordination members at the surface. Its spectrogram is then processed to correct for atomic number (Z), absorption (A), and fluorescence effects (F). After these ZAF corrections are applied the quantitative analyses were as follows:

1. Sample 1a - Magnesium Aluminum Silicate - $(MgAl_2Si_2O_4)_n$
   Particle size: 250-300 microns
   Spectrum, overall: Atomic %:
   Al: 33.65
   Si: 65.19
   Ti: 1.99

Sample 1b - Magnesium Aluminum Silicate - $(MgAl_2Si_2O_4)_n$
   Particle size: 2-3 microns
   Spectrum, overall: Atomic %:
   Mg: 4.02
   Al: 31.90
   Si: 60.35
   S: 2.04
   Ca: .47
   Ti: 1.23

These findings show that the magnesium-containing phase is present in the microfine-grained portion of the clay in the form of a surface bound brucite-type coordination. The presence of sulfur presumed to be sulfates or sulfites accounts for the higher than usual solubility of magnesium.

| | | |
|---|---|---|
| 2. | Sample 2a - | Magnesium Aluminum Silicate (Commercial Veegum, R. T. Vanderbilt Co., Inc.) Particle size: 250–300 microns |
| | Sample 2b - | Magnesium Aluminum Silicate Microfine grind of Sample 2a Particle size: 1-2 microns Spectrum, Spot: Atomic %: |
| | | Mg: 8.37 |
| | | Al: 13.20 |
| | | Si: 73.26 |
| | | Cl: .44 |
| | | K: .92 |
| | | Ca: 2.05 |
| | | Fe: 1.76 |
| 3 | Sample 3 - | Kaolin Particle size: 0.5–3 microns Spectrum, Spot: Atomic %: |
| | | Al: 40.42 |
| | | Si: 57.31 |
| | | Ti: .97 |
| | | Fe: 1.30 |

B. Free Magnesium—Prior to spectra analysis all samples were initially tested in the clinic on seventeen patients with the following results:

| | |
|---|---|
| Sample 1a: | clinically non-responsive |
| 1b: | 100% clinically responsive |
| 2a: | clinically non-responsive |
| 2b: | 100% clinically responsive |
| 3: | clinically non-responsive |

Alumina silicates that have no exposed surface magnesium on gross particles are clinically non-responsive. Reducing the gross particles size from 250-300 microns to a microfine grind of 0.5-3 microns produces 100% positive clinical results provided magnesium exists on the crystalline surface in the form of a gibbsite-type or brucite-type arrangement. Under such circumstances, the magnesium will disassociate in accordance with Equation (6).

One-half gram of samples 1b, 2b and 3 were mixed in 100 ml. of distilled water and then measured for total magnesium by atomic adsorption spectroscopy. It is recognized that the results could be the sum of combined and free magnesium.

| | |
|---|---|
| Clay Sample 1b: | 25.3 ppm magnesium |
| 2b: | 3.3 ppm magnesium |
| 3: | .74 ppm magnesium |

Samples 1b, 2b and 3 were then added into a 22.0/71.5 water/ethanol solution in accordance with proportions set forth in the above Examples. It should be obviously apparent that reducing the water by 78% reduces the source of hydrogen exchange ions. After allowing to settle for 24 hours, the supernatant was drawn and centrifuged at 1500 rpm for 15 minutes and again measured by atomic adsorption spectroscopy with the following results:

| | |
|---|---|
| Clay Sample 1b: | 16.8 ppm free magnesium |
| 2b: | 4.6 ppm free magnesium |
| 3: | 0 ppm free magnesium |

These samples were then measured for free magnesium with an Ion Selective Electrode (ISE) meter and ISE probe with the following results:

| | |
|---|---|
| Clay Sample 1b: | 28.0 ppm free magnesium |
| 2b: | 4.5 ppm free magnesium |
| 3: | .72 ppm free magnesium |

Within the experimental error of the measurements it is clearly established that magnesium disassociates in the form of cations in certain alumina silicates.

Six ml of 23.4% conc. of sodium chloride solution was then added to the 100 ml solutions of water and water/ethanol solution containing clay samples 1b and 2b with the sodium being an additional source of exchange cations for the clay-contained magnesium. The supernatant was drawn off and centrifuged at 1500 rpm for 15 minutes and then measured for free magnesium using atomic adsorption spectroscopy.

| | | |
|---|---|---|
| Water: | Clay sample 1b: | 49.2 ppm free magnesium |
| | Clay sample 2b: | 5.9 ppm free magnesium |
| Water/ethanol: | Clay sample 1b: | 19.9 ppm free magnesium |
| | Clay sample 2b: | 4.7 ppm free magnesium |

C. $OH^-$ Analysis—To support Equation (6) and further corroborate Equatin (5), a solution of 30 ml water and 70 ml ethanol was adjusted with 2 cc of 4M KCl and its qualitative reference pH was determined to be 7.29. Using a magnetic mixer and with pH probe in place, one-half gm of clay sample 1b was added to the solution. The pH increased to 8.30.

Toxicity Tests—A comparative, repeated application of a dermal-irritation study was conducted on three male and three female albino rabbits comparing the preparation of Example 1 with commercially available Vitalis as a control.

There was one intact skin and one abraded skin test site for each test material on each rabbit. Each application site was treated with 0.5 ml of each solution. The rabbits were treated and then occluded for six hours on each of five consecutive days. Observations for skin irritation were made at 6 and 24 hours after each application.

Each was scored according to the following scale:

| Range of Values | Degree of Dermal Irritation |
|---|---|
| 0 | Non-irritating |
| .1–.5 | Minimally irritating |
| .6–1.5 | Slightly irritating |
| 1.6–3.0 | Mildly irritating |
| 3.1–n8.0 | Moderately irritating to n extremely irritating |

The preparation of Example 1 was slightly irritating and produced a dermal irritation score of .92. Vitalis was mildly irritating and produced a score of 1.78.

E. Delivery of the Ion Products—The epidermis is relatively impermeable to surface-applied liquids. Because normal epidermis is negatively charged, the magnesium cations of the compositions of the present invention are electrically attracted and have somewhat of a chance of penetrating the epidermis. The actual route, however, for both the cations and the hydroxyl anions is via the follicular canal, into and through the sebaceous gland and onto the basale lamina. In addition to causing hydrolysis of the water to produce hydroxyl anions as described earlier, the secondary function of the ethanol, being fat-soluble, is to facilitate this passage and act as the carrier of the magnesium cations and hydroxyl anions to the sites of need which will be described later. The ability of the compositions of the present invention, with and without sulfur, using ethanol to deliver the ion products resulting in 100% positive cure of dandruff, seborrheic and scalp psoriasis in clinical patients is later described. In-vivo, pre- and post-treatment electron micrographs clearly show a diseased cellular conformation being returned to normal after three topical applications. Substituting isopropyl alcohol for ethanol in the present compositions renders them clinically nonresponsive.

As an ancillary corroboration of compositions of the present invention being able to penetrate to the sebaceous gland and carry and deliver a substance, a small amount of minoxidil was added to the 100 ml preparation of Example 1. Four clinically bald males were instructed to apply the mixture once daily. While the manufacturer of minoxidil reports vellus hair appearance in 30–50% of the samples in 4–6 months, the instant preparation with minoxidil produced vellus hair on the four samples within nine days.

In addition to its epidermal penetrating ability the preferential adsorption of the ethanol has the equivalency of slow evaporation, gradually changing the compositions of the present invention to a water-rich component which in turn alters the pH upwardly. This results in the establishment of a varied pH producing a gradient that assists in the assurance of cellular uptake.

F. Clinical Trials—Clinical trials were conducted by a noted dermatologist who has been in practice for 22 years. He is associated with the consulting staff of the Beverly Hospital, Massachusetts and with the regular staff of the Massachusetts General Hospital. Twenty-seven desperation cases having the named scalp disorders were treated with a total of 60 ml of the preparation of Example 1, allowing about 3/5 every-other-day topical self-applications.

Every case was 100% responsive. The dermatologist's report stated that the present treatment is more effective than any available standard therapy. The efficacious term of positive response after applying 60 ml ranged from 8 to 12 weeks. After this period, without maintenance, any return of the described disease symptoms is attributed to a patient's inability to assimilate magnesium.

G. Pathological Analysis

1. Tissue—Epidermis/Dermis:

Tissue clinically observed to be moderately involved with seborrheic dermatitis was treated with the preparation of Example 2 containing 0.1 gm of precipitated sulfur. The treatment consisted of topically applying approximately 10–15 ml of this preparation twice, the second application occuring 48 hours after the first. Ten days after the initial application, one-quarter inch punch biopsies were performed on the affected/treated area and contiguous affected/untreated area. The tissue was then prepared for light and electron microscopy.

The treated tissues demonstrated, by the light microscopy in plastic-embedded thin sections, the sebum within the hair follicles to appear uniform in composition, suggestive of liquid content. The vacuoles within the sebaceous glands of the treated tissue demonstrated a more uniform appearance, demonstrating a nearly consistent spherical configuration. By light microscope in plastic-embedded tissue, the untreated tissue demonstrated a more granular sebum within the hair follicles. By electron microscopy the treated tissues showed a wavy basement membrane with the demonstration of stratum basale, as the untreated tissue demonstrated a flat basement membrane and loss of the usual delicate stratum basale. Electron microscopy examination suggested that in the treated tissues, only the peripheral epithelial cells within the sebaceous gland were spared of vacuoles. Progressively, the vacuoles became larger and more numerous toward the center of the sebaceous gland. For the most part, only a signle layer of peripheral cells appear to be devoid of vacuoles. In the untreated tissue, there were multilayers of peripheral epithelial cells without vacuolation. The vacuoles in the untreated tissue showed a much greater variation of shape and size through their distribution and demonstrated a coarse reticulated appearance in addition to areas of a more liquid-appearing composition. Within the untreated tissues, the sebum and secretions within the sebaceous gland shows a crystalline composition, presumed to represent cholesterol. The electron microscopic findings of the crystalline composition within the sebaceous gland vacuoles, and the reticulated arrangement within the secretions appear to correlate with the granular composition to the sebum noted within the hair follicles.

2. Sebaceous Cell Mitochondria:

Tissue clinically observed to be moderately involved with seborrheic dermatitis was treated with the preparation of Example 2 containing 0.1 gm of precipitated sulfur. The treatment consisted of topically applying approximately 10–15 ml of this preparation twice, the second application occurring 48 hours after the first. Ten days after the initial application, one-quarter inch punch biopsies were performed on affected/untreated, and affected/treated areas. The samples were then prepared for electron microscopy reviewing.

The prints of before-treatment show the secretions having a heterogeneous composition with the presence of crystalline particles, reticulated-appearing substance and the more typical homogeneous portion of liquid-appearing substance. Several features become quite apparent, with the most striking feature different between before- and after-treatment being the invagination of cytoplasm "pinocytosis" within the mitochondria. This process is noted at various phases and demonstrated with section in various directions, showing the invagination of the peripheral membranes with varying degrees of imbibement of cytoplasm within the mitochondria. This is characterized in most areas by the demonstration of duplication of the membranes from two to four—a conformation never before identified in any literature. Occasional mitochondria show elongation and an attenuation of the mid-portion of the mitochondria, suggesting division or duplication of the mitochondria. The attenuation in some sections is so marked that there appears to be an absence of matrix in the mid-portion of the mitrochondria. An attempt to demonstrate degenerative changes within the mitochondria reveals that there appears to be edema in the matrix region of the mitochondria. In several of the prints, there is a high degree of cytoplasmic vacuolation seen to a greater degree in post-treatment prints. Study of mitochondria in the sebaceous cells before and after treatment reveals the observation in the pretreatment mitochondria which shows a marked degree of pinocytotic imbibement of cytoplasm. This observation is made at various stages of development and can be readily demonstrated in the electron microscopy prints. The explanation of this observation is not available in any reference material or literature. The enhancement of pinocytosis has been described in the literature with increased hydrogen ions on membranes.

3. Sebaceous Cells:

Tissue clinically observed to be moderately to heavily involved with seborrheic dermatitis was treated with the preparation of Example 2 containing 2.0 gms precipitated sulfur. Treatment consisted of twice topically applying approximately 10-15 ml of the preparation, the second application occurring 48 hours after the first. Ten days after the intial application, one-quarter inch punch biopsies were performed on unaffected/untreated, affected/untreated and affected/treated tissue. The samples were then prepared for electron microscopy viewing.

The clinically normal skin and the skin treated with the present sulfur-containing preparation show findings which are essentially the same. The normal skin shows intracellular demarcations and apparent homogeneous-appearing composition, consistent with liquid content. The skin treated with the present preparation shows the sebaceous material within the cells to display somewhat larger accumulations, but with relatively homogeneous-appearing sebaceous material, essentially free of crystalline or reticulated-appearing particles. The untreated skin demonstrates markedly variable enlarged droplets of sebaceous material within the cells, showing a high degree of crystalline and particulate matter throughout the sebaceous material.

Tissue clinically observed to be moderately to heavily involved with seborrheic dermatitis was treated with the preparation of Example 1, containing no precipitated sulfur. The treatment consisted of topically applying 10-15 ml of this preparation thrice—each application being separated by 48 hours. Ten days after the initial application, a one-quarter inch punch biopsy was performed on the affected/treated area. The sample was then prepared for electron microscopy viewing.

Tissue examination with sections mounted in plastic shows skin with hair follicles and sebaceous glands present. Within the hair follicles, hair shafts are identified and some sebum is noted, the consistency of which appears to be somewhat variable in content. In some of the follicles the sebaceous material appears to be crystalline or reticulated, whereas in other follicles it appears to be more homogeneous and more uniformly distributed around the hair shaft. Discrete vacuoles of sebum within many of the cells are revealed. Although most of the sebum vacuoles appear to be homogeneous and liquid, in others there appear to be some degree of crystalline material and a reticulated composition to the sebum. Mitochondria within the sebaceous gland epithelial cells in proximity to the sebaceous material displays preservation of the usual appearance, with perhaps a moderate degree of elongation without evidence of engulfment of cytoplasm within the mitochondria. The ultrastructural findings with the preparation of Example 2, devoid of sulfur content, show a clinical response which suggests return to normal status. The thin plastic sections show some follicles to demonstrate apparently normal sebum, with occasional focus showing a more crystalline-appearing substance. Sebaceous gland vacuolation more closely resembles that of the normal sebaceous gland, with discrete vacuoles of liquid-appearing sebum. In rare foci, the sebum shows a slight degree of reticulation and crystallization similar to that noted in seborrheic dermatitis. Mitochondria are essentially unremarkable and resemble that of the normal mitochondria of the sebaceous glands. The use of the present preparation devoid of sulfur content demonstrates a clinical response either as a result of the delivery system and/or its pH influence on the follicles and sebaceous glands. Clinically, the scales had disappeared and the skin had returned to a normal appearance. Ultrastructure findings suggest response to treatment with return to normal appearance. The residual crystalline material within some of the follicles and in rare vacuoles within the sebaceous glands suggests an incomplete clearance of the particulate sebum with the absence of sulfur.

4. Effect on Unaffected Tissue:

Tissue of a left and right scapula was clinically observed to be normal. The right scapula was over-treated four times daily for six days with the preparation of Example 2 containing 0.1 gm precipitated sulfur. The left scapula was untreated. Ten days after the initial application, one-quarter inch biopsies were performed from each area and the samples were prepared for light microscopy. There were no significant differences between the two slides. The sebaceous glands remain essentially identical. The over-treated right scapula specimen demonstrated the presence of infiltrate, the untreated left scapula specimen demonstrated none.

Those knowledgeable in biochemistry art will agree the described scalp disorders must be the result of a metabolic anomaly. It is beyond the scope of this invention to discuss the specifics of anabolism and catabolism that result in hyperproliferation of epidermal and sebaceous gland cells. It is important to understand that the rate of catabolism of a cell is not controlled by the concentration of its nutrients but rather by its instant-to-instant needs for energy. The simplest type of regulation involves the basic parameters affecting enzymatic reactions. Each enzyme of a sequence requires a characteristic pH, a characteristic affinity for its substrate(s) and products(s) and a characteristic affinity for its co-enzyme or metal-ion activator. Oxidative phosphorylation requires the presence of certain transferases and, in particular, phosphohycholases and phosphotransferases require $Mg^{++}$ as co-factors. The successful results of the compositions of the present invention are based on an original postulation that each covering epithelia cell has a definitive functional life that may be equal to or less than its generally defined real time life. The constantly phosphorylating and imbibing mitochondria of electron microscope-viewed pretreatment fields can be concluded to cause a shorter functional life of the cell and early necrosis resulting in rapidly accelerated replacement or hyperproliferation. Summarily, the absence or insufficient amount of $Mg^{++}$ to the pathological sites reverses these adverse events and restores the tissue to normal morphology. It has been determined that when $Mg^{++}$ cations and $OH^-$ anions are delivered to the affected sites a normal rate of cellular turnover. As described earlier, pinocytotic activity has been associated with excessive hydrogen ions on the outer wall of the membrane of the mitochondria. The $OH^-$ anions released by the present compositions easily penetrate the cellular wall and combine with the $H^+$ of the mitochondria to form water. This step is instrumental in restoring normalcy to the oxidation phosphorylation process. The lines of evidence in this invention result in solid medical conclusions and nonprovocative results.

Ancillary corroboration is offered by the public announcement of June 6, 1985, 13 months subsequent to the filing of application Ser. No. 606,975 on May 4, 1984, now abandoned, confirming the causative factor of Toxic Shock Syndrome as being the absorption of magnesium from cavity epithelia by certain magnesium-absorbing polyester fibers. Eliminating this particular fiber had the equivalency of adding magnesium.

It should be understood that there may be various changes and modifiecations of the example herein chosen for purposes of disclosure without departing from the spirit and scope of the invention. Accordingly, the foregoing illustrations are not to be interpreted as restrictive of the invention beyond that necessitated by the following claims.

We claim:

1. A composition for treating dandruff, seborrheic dermatitis and scalp psoriasis comprising an effective amount of a combination of ingredients consisting of about 0.35–0.65 gm of microfine particles of magnesium aluminum silicate having an average particle size of 0.5–3 microns, about 16.5–27.5% by volume of water, about 53.5–89.5% by volume of ethanol and about 4.5–7.5% by volume of a concentrated aqueous solution of sodium chloride based on a 100 ml preparation.

2. The composition according to claim 1 wherein the 100 ml preparation consists of 0.5 gm of magnesium aluminum silicate; 22% by volume of water; 71.5% by volume of ethanol and 6% by volume of the concentrated aqueous solution of sodium chloride.

3. The composition according to claim 2 wherein the 100 ml preparation includes 0.1–2 gms of precipitated sulfur.

4. The composition according to claim 2 wherein the solution of sodium chloride is a 23.4% concentrated aqueous solution.

5. The composition according to claim 1 wherein the combination of ingredients includes an emollient.

6. The composition according to claim 5 wherein the emollient is glycerin.

7. The composition according to claim 1 wherein the combination of ingredients includes a keratolytic agent.

8. The composition according to claim 7 wherein the keratolytic agent is precipitated sulfur.

9. The composition according to claim 1 whrein the 100 ml preparation includes 1–3 drops of glycerin.

10. The composition according to claim 1 wherein the 100 ml preparation includes 0.05–2.5 gms of precipitated sulfur.

11. The composition according to claim 1 wherein the solution of sodium chloride is a 23.4% concentrated aqueous solution.

12. A composition for treating dandruff, seborrheic dermatitis and scalp psoriasis comprising an effective amount of a combination of ingredients consisting of about 0.35–0.65 gm of microfine particles of magnesium alumina silicate having an average particle size of 0.5–3 microns; 16.5–27.5% by volume of distilled water; 53.5–89.5% by volume of ethanol; 4.5–7.5% by volume of a 23.4% aqueous solution of sodium chloride and 1–3 drops of glycerin based on a 100 ml preparation.

13. The composition according to claim 12 wherein the combination of ingredients includes 0.05–2.5 gms of precipitated sulfur.

14. A method for the treatment of dandruff, seborrheic dermatitis and scalp psoriasis which comprises topically applying to the scalp epidermis an effective amount of the composition according to claim 1.

15. A method for treating dandruff, seborrheic dermatitis and scalp psoriasis which comprises topically applying to the scalp epidermis an effective amount of the composition according to claim 12.

16. A method for treating dandruff, seborrheic dermatitis and scalp psoriasis which comprises topically applying to the scalp epidermis an effective amount of the composition according to claim 13.

* * * * *